United States Patent
Bevot et al.

(10) Patent No.: US 12,429,453 B2
(45) Date of Patent: Sep. 30, 2025

(54) EVALUATION AND CONTROL UNIT FOR A GAS SENSOR

(71) Applicants: Robert Bosch GmbH, Stuttgart (DE); Melexis Technologies NV, Tessenderlo (BE)

(72) Inventors: Claudius Bevot, Stuttgart (DE); Bernhard Ledermann, Stuttgart (DE); Stefan Kremer, Stuttgart (DE); Volodymyr Sotnikov, Tessenderlo (BE)

(73) Assignees: Robert Bosch GmbH, Stuttgart (DE); Melexis Technologies NV, Tessenderlo (BE)

( * ) Notice: Subject to any disclaimer, the term of this patent is extended or adjusted under 35 U.S.C. 154(b) by 480 days.

(21) Appl. No.: 17/905,515

(22) PCT Filed: Mar. 5, 2021

(86) PCT No.: PCT/EP2021/055573
§ 371 (c)(1),
(2) Date: Sep. 2, 2022

(87) PCT Pub. No.: WO2021/176046
PCT Pub. Date: Sep. 10, 2021

(65) Prior Publication Data
US 2023/0121579 A1    Apr. 20, 2023

(30) Foreign Application Priority Data

Mar. 6, 2020 (EP) .................................... 20161475

(51) Int. Cl.
*G01N 27/406* (2006.01)
*G01N 27/409* (2006.01)
(Continued)

(52) U.S. Cl.
CPC ....... *G01N 27/4065* (2013.01); *G01N 27/409* (2013.01); *G01N 27/4163* (2013.01); *G01N 33/0027* (2013.01); *G01R 31/52* (2020.01)

(58) Field of Classification Search
CPC ............. G01N 27/4065; G01N 27/409; G01N 27/4163; G01N 33/0027; G01R 31/52
See application file for complete search history.

(56) References Cited

U.S. PATENT DOCUMENTS

2007/0261475 A1* 11/2007 Allmendinger ...... G01N 27/419
73/31.05
2012/0293183 A1   11/2012 Ledermann
(Continued)

FOREIGN PATENT DOCUMENTS

DE    102008001697 A1    11/2009
DE    102010000663 A1    7/2011
(Continued)

OTHER PUBLICATIONS

Reif, Sensoren im Kraftfahrzeug, 1. edition 2010, pp. 160-165 with machine translation., 12 pages, Jan. 1, 2010.

*Primary Examiner* — Stephanie E Bloss
*Assistant Examiner* — Michael A Harrison
(74) *Attorney, Agent, or Firm* — Woodard, Emhardt, Henry, Reeves & Wagner LLP

(57) ABSTRACT

An evaluation and control unit (100) for a broadband lambda probe (200) and a method for operating the same are disclosed. The evaluation and control unit (100) comprises pins (RE, IPE, APE, MES) connectable to electrical wires (201, 202, 203, 204) of electrochemical cells (210, 211) of the broadband lambda probe (200), a controller (103), a ASIC reference potential source (102), wherein the ASIC reference potential source (102) is operable by means of the controller (103), a switch assembly (104) connected to each of the pins (RE, I PE, APE, MES), wherein the switch assembly (104) comprises a first transistor ($T_{Wire}$) and a second transistor ($T_{ECU}$), wherein the switch reference potential source (105) is connected to a gate side of the first and second transistors ($T_{Wire}$, $T_{ECU}$), wherein the controller (103) is configured to vary the switch reference potential ($V_{SW}$) applied to the gate side of the first and second transistors ($T_{Wire}$, $T_{ECU}$), wherein the switch assembly (104) is configured to allow a limiting current flowing to the drain side of the first transistor ($T_{Wire}$) from the ASIC reference potential if the potential at the gate side of the first and second transistors ($T_{Wire}$, $T_{ECU}$) is at a predetermined voltage between values of an open and closed switch.

7 Claims, 4 Drawing Sheets

(51) Int. Cl.
*G01N 27/416* (2006.01)
*G01N 33/00* (2006.01)
*G01R 31/52* (2020.01)

(56) References Cited

U.S. PATENT DOCUMENTS

2013/0234744 A1 9/2013 Carbonaro et al.
2018/0246157 A1* 8/2018 Zarabadi ................ G01R 1/203
2021/0372964 A1* 12/2021 Matsushita .......... G01N 27/419

FOREIGN PATENT DOCUMENTS

DE 102011007068 A1 10/2012
EP 2277035 B1 11/2016

* cited by examiner

EVALUATION AND CONTROL UNIT FOR A GAS SENSOR

PRIOR ART

In order to detect characteristics of gases, several sensor types are known. One example is a lambda probe which is used to detect characteristics of the exhaust of an internal combustion engine. Such lambda sensors or probes are known from Konrad Reif (Hrsg.): Sensoren im Kraftfahrzeug, 1. edition 2010, pages 160-165, for example.

A control unit for the operation of a broadband lambda probe is described in German Patent Application No. DE 10 2008 001 697 A1. "Operation" encompasses in particular control of the lambda probe, as well as evaluation of the signals or data supplied by the lambda probe. The control unit encompasses a signal conditioning unit, an analog/digital (A/D) converter, a pump current controller, a digital interface, a controller, a pump current source, an internal pump electrode terminal, an external pump electrode terminal, and a reference electrode terminal. The signal conditioning unit is provided in order to ascertain an actual value for the pump current controller, and to ascertain further information regarding the operating state of the broadband lambda probe. The further information regarding the operating state of the broadband lambda probe is outputtable via the digital interface. A corresponding control unit, in the form of an integrated circuit (IC) for controlling broadband lambda probes suitable for diesel and gasoline engines, is marketed by the Applicant under the designation "CJ135".

A plurality of further control units specialized for a particular application are encountered nowadays in internal combustion engines or in motor vehicles equipped with such internal combustion engines. An internal combustion engine is furthermore operated, in a conventional manner, by way of an engine control device. These control units or control devices possess analog and digital inputs that in part also provide additional functions such as a pull-up/pull-down structure, or a voltage divider required, for example, for the evaluation of temperature sensors. The evaluation circuits on which these are based can be made up of discrete components or, by combining multiple inputs and outputs, of individual application-specific integrated circuits (ASICs).

The semiconductor building-up the ASIC only works in a certain voltage range. Outside this voltage range, structures meant to be insulating can become conducting or permanently damaged. Below the lowest voltage, i.e. its ground voltage, the structure has to be protected, hindering its original functionality. In particular, such a structure for operating a wide band lambda sensor as described in DE 10 2011 007 068 A1 is known from DE 10 2010 000 663 A1 or EP 2 277 035 B1, which contains wires electrically connected to the evaluation and control units. Currently, diagnosis of the electrical wires of the wide band lambda sensor are not complete with respect to the detection of short circuits. Attempts have been made to improve especially the pin-pointing of the diagnosis such as described in US2013/0234744 A1.

Despite the advantages provided by the above devices and methods for detecting short circuits, there is still potential for improvements. Particularly, the above devices and methods have so far proved not to be robust. Especially detection of short circuit to voltages below the ECU ground voltage are incomplete due to the limitation of the technology mentioned above. Such voltages can appear at usually short circuit to ground demonstration, since there the wire is connected to the ground of the vehicle. It differs from the ECU ground voltage of the ASIC due to leakage currents from other components and the spatial distance between ECU and the vehicle ground connection. In case a short circuit to ground is applied, i.e. a low out-of-range fault, the analysis with conventional devices is hindered by the wish to protect the internal hardware. In particular, for cold sensors the ECU only needs to be protected against voltages at the wire, where the short circuit pin is applied. However, due to couplings between the wires, e.g. by capacitors or former warm sensor, similar voltages exists at each wire. Thus, typically all wires are disconnected from the evaluation circuit. In contrast to the direct short circuit connection, these coupling effects can be temporary with the proper circuitry. Nevertheless, they hinder to pin-point the short circuit to the corresponding wire due to the activated common hardware protection.

SUMMARY

Thus, an evaluation and control unit for a gas sensor, particularly a broadband lambda probe, and a method for operating the same are disclosed which aim to reduce the disadvantages provided by the above described devices and methods and which particularly allow for a pin-pointing to UEGO (Universal Exhaust Gas Oxygen) signal wire specific entries.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

The control and evaluation unit according to the present invention, preferably embodied as an ASIC, is universally usable for the operation and evaluation of a gas sensor such as a broadband lambda probe. Nevertheless, the control and evaluation unit as disclosed herein is applicable to any type of gas sensor such as a NOx-sensor. The control and evaluation unit comprises pins connectable to electrical wires of electrochemical cells of the gas sensor, a controller, an ASIC reference source, wherein the ASIC reference source is operable by means of the controller, a switch assembly connected to each of the pins, wherein the switch assembly comprises at least a first transistor, wherein a switch reference source is connected to a gate side of the first transistor and the ASIC reference source is connected to the source side of the first transistor, wherein the controller is configured to vary a switch reference potential applied to the gate side of the first transistor, wherein the switch assembly is configured to allow a limited current flowing to the drain side of the first transistor from the ASIC reference source if the potential at the gate side of the first transistor is at a predetermined voltage between values of an open and closed switch over the potential at the source side of the first transistor.

The ASIC reference source and or the switch reference source may be a potential source or a current source.

The controller may be configured to switch the ASIC reference potential provided by the ASIC reference source to a value larger than the ground of the controller while the switch assembly is in an open state.

The controller may be configured to put the first transistor in a linear mode by varying the switch reference potential in relation to a source potential of the first transistor.

The term "linear mode" as used herein may refer to a mode of a transistor wherein it is neither fully conducting nor fully open, but acts as a current source or a very high resistance. This means it allows a flowing current, which is much smaller as it would be in the conducting state. Particularly, in the linear mode current is independent from drain-source voltage. This enables of charging or discharging externally structures like capacitors with time.

The evaluation and control unit may further comprise at least one comparator, wherein the controller may be configured put the switch assembly in an open state if a short circuit to ground is detected by the comparator.

The comparator may be configured to detect a short circuit to ground presence or absence at one of the pins if the ASIC reference potential is raised and a potential at that pin exceeds a comparator threshold. If, at one of the pins when the ASIC reference potential is raised, the potential at that pin exceeds a comparator threshold, a short circuit to ground is present. Particularly, if the ASIC reference potential is raised, some comparators will show that there is short-circuit to ground but other comparators will show that there is no short-circuit.

The switch assembly may further comprise a second transistor, wherein the switch reference source is connected to a gate side of the second transistor and the ASIC reference source is connected to the source side of the second transistor.

The method for operating an evaluation and control unit according to the present invention comprises the following steps:

varying the switch reference potential applied to the gate side of the first transistor, in order to allow a limited current flowing to the drain side of the first transistor from the ASIC reference source if the potential at the gate side of the first transistor is at a predetermined value between values of an open and closed switch over the potential at the source side of the first transistor.

The method may further comprise switching the ASIC reference potential to a value larger than the ground of the controller while the switch assembly is in an open state.

The method may further comprise putting the first transistor in a linear mode by varying the switch reference potential in relation to a source potential of the first transistor.

The method may further comprise detecting a short circuit to ground presence or absence by means of at least one comparator and putting the switch assembly in an open state if the short circuit to ground at one of the pins is detected.

The method may further comprise raising the ASIC reference potential and detecting a potential at one of the pins, wherein a short circuit to ground presence or absence is detected. If, at one of the pins when the ASIC reference potential is raised, the potential at that pin exceeds a comparator threshold, a short circuit to ground is present. Particularly, if the ASIC reference potential is raised, some comparators will show that there is short-circuit to ground but other comparators will show that there is no short-circuit.

Further, a computer program is disclosed that is configured to carry out each of the steps of the method.

Further, an electronic storage device is disclosed, on which such a computer program is stored.

Furthermore, an electronic control unit is disclosed which comprises such an electronic storage device.

The present disclosure further discloses and proposes a computer program including computer-executable instructions for performing the method according to the disclosed method/device/system in one or more of the embodiments enclosed herein when the program is executed on a computer or computer network. Specifically, the computer program may be stored on a computer-readable data carrier. Thus, specifically, one, more than one or even all of the method steps as indicated above may be performed by using a computer or a computer network, preferably by using a computer program.

The present disclosure further discloses and proposes a computer program product having program code means, in order to perform the method according to the disclosed method/system in one or more of the embodiments enclosed herein when the program is executed on a computer or computer network. Specifically, the program code means may be stored on a computer-readable data carrier.

Further, the present disclosure discloses and proposes a data carrier having a data structure stored thereon, which, after loading into a computer or computer network, such as into a working memory or main memory of the computer or computer network, may execute the method according to one or more of the embodiments disclosed herein.

The present disclosure further proposes and discloses a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the present disclosure proposes and discloses a modulated data signal which contains instructions readable by a computer system or computer network, for performing the method according to one or more of the embodiments disclosed herein.

Preferably, referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the present disclosure further discloses:
A computer or computer network comprising at least one processor, wherein the processor is adapted to perform the method according to one of the embodiments described in this description,
a computer loadable data structure that is adapted to perform the method according to one of the embodiments described in this description while the data structure is being executed on a computer,
a computer program, wherein the computer program is adapted to perform the method according to one of the embodiments described in this description while the program is being executed on a computer,
a computer program comprising program means for performing the method according to one of the embodiments described in this description while the computer program is being executed on a computer or on a computer network,
a computer program comprising program means according to the preceding embodiment, wherein the program means are stored on a storage medium readable to a computer,
a storage medium, wherein a data structure is stored on the storage medium and wherein the data structure is adapted to perform the method according to one of the embodiments described in this description after having been loaded into a main and/or working storage of a computer or of a computer network, and
a computer program product having program code means, wherein the program code means can be stored or are stored on a storage medium, for performing the method according to one of the embodiments described in this description, if the program code means are executed on a computer or on a computer network.

Summarizing the findings of the present disclosure, the following embodiments are disclosed:

Embodiment 1: Evaluation and control unit for a gas sensor, particularly a broadband lambda probe, comprising:
pins connectable to electrical wires of electrochemical cells of the gas sensor, a controller,
an ASIC reference source, wherein the ASIC reference source is operable by means of the controller,
a switch assembly connected to each of the pins, wherein the switch assembly comprises at least a first transistor, wherein a switch reference source is connected to a gate side of the first transistor and the ASIC reference source is connected to the source side of the first transistor, wherein the controller is configured to vary a switch reference potential applied to the gate side of the first transistor, wherein the switch assembly is configured to allow a limited a current flowing to the drain side of the first transistor from the ASIC reference source if the potential at the gate side of the first transistors is at a predetermined voltage between values of an open and closed switch over the potential at the source side of the first transistor.

Embodiment 2: Evaluation and control unit according to the preceding embodiment, wherein the controller is configured to switch the ASIC reference potential provided by the ASIC reference source to a value larger than the ground of the controller while the switch assembly is in an open state.

Embodiment 3: Evaluation and control unit according to the preceding embodiment, wherein the controller is configured to put the first transistor in a linear mode by varying the switch reference potential in relation to a source potential of the first transistor.

Embodiment 4: Evaluation and control unit according to any preceding embodiment, further comprising at least one comparator, wherein the controller is configured put the switch assembly in an open state if a short circuit to ground is detected by the comparator.

Embodiment 5: Evaluation and control unit according to the preceding embodiment, wherein the comparator is configured to detect a short circuit to ground presence or absence at one of the pins if the ASIC reference potential is raised and a potential at that pin exceeds a comparator threshold.

Embodiment 6: Evaluation and control unit according to any of the preceding embodiments, wherein the switch assembly further comprises a second transistor, wherein the switch reference source is connected to a gate side of the second transistor and the ASIC reference source is connected to the source side of the second transistor.

Embodiment 7: Method for operating an evaluation and control unit according to any preceding embodiment, comprising the following steps:
varying the switch reference potential applied to the gate side of the first transistor, in order to allow a limited current flowing to the drain side of the first transistor from the ASIC reference source if the potential at the gate side of the first transistor is at a predetermined value between values of an open and closed switch over the potential at the source side of the first transistor.

Embodiment 8: Method according to the preceding embodiment, further comprising switching the ASIC reference potential to a value larger than the ground of the controller while the switch assembly is in an open state.

Embodiment 9: Method according to the preceding embodiment, further comprising putting the first transistor in a linear mode by varying the switch reference potential in relation to a source potential of the first transistor.

Embodiment 10: Method according to any of the three preceding embodiments, further comprising detecting a short circuit to ground by means of at least one comparator and putting the switch assembly in an open state if the short circuit to ground at one of the pins is detected.

Embodiment 11: Method according to any of the four preceding embodiments, further comprising raising the ASIC reference potential and detecting a potential at one of the pins, wherein a short circuit to ground presence or absence at the one pin is detected.

Embodiment 12: Computer program configured to carry out each of the steps of the method according to any one of embodiments 7 to 11.

Embodiment 13: Electronic storage device, on which a computer program according to the preceding embodiment is stored.

Embodiment 14: Electronic controller, comprising a storage device according to the preceding embodiment.

It shall be understood that a preferred embodiment of the invention can also be any combination of the dependent claims or above embodiments with the respective independent claim.

BRIEF DESCRIPTION OF THE DRAWINGS

Further optional features and embodiments will be disclosed in more detail in the subsequent description of embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

In the Figures.

DETAILED DESCRIPTION

Figure 1:
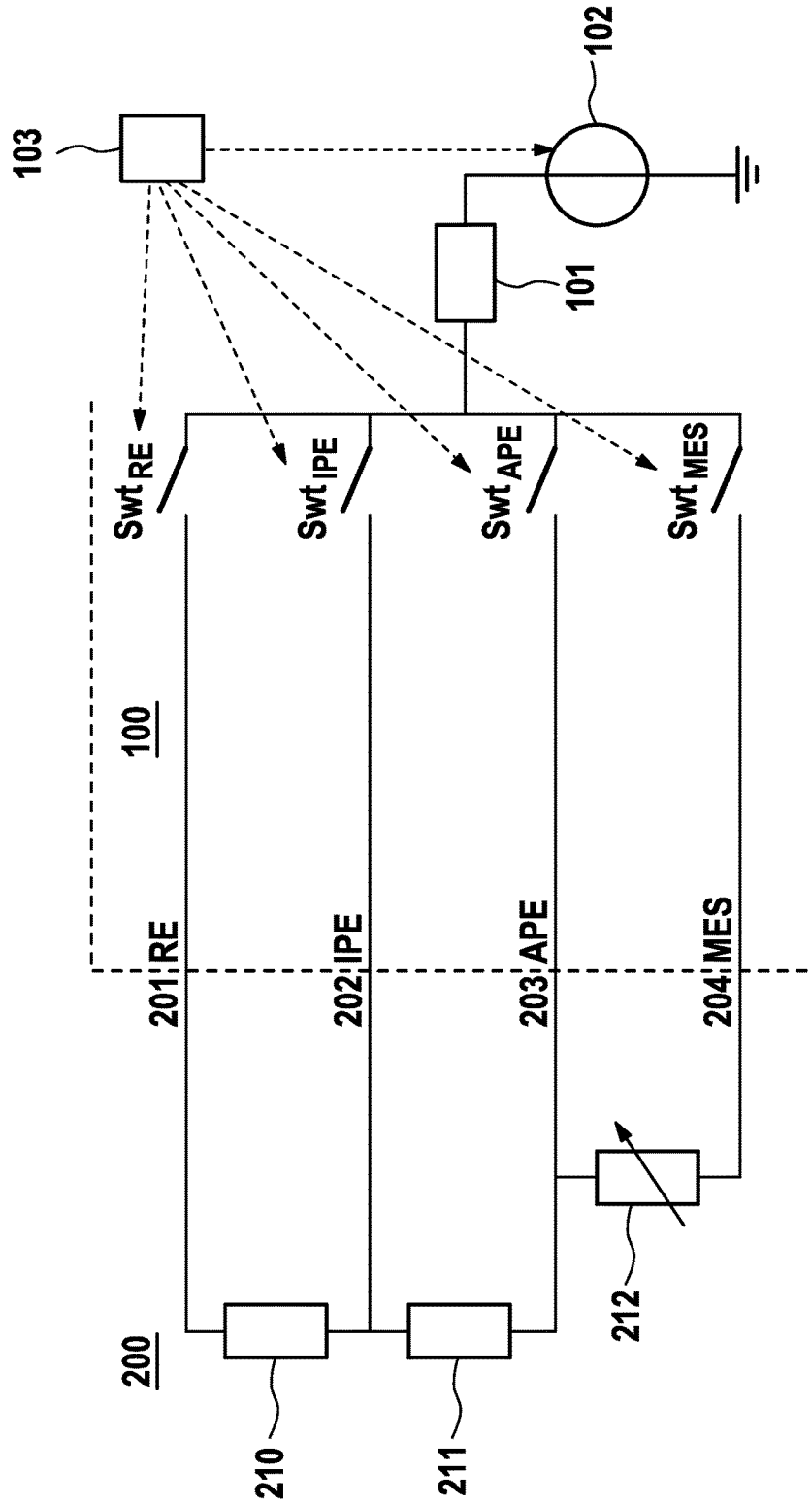
FIG. 1 shows an evaluation and operation unit.

FIG. 1 shows an exemplary embodiment of the evaluation and operation unit 100. The evaluation and operation unit 100 is configured to operate a gas sensor 200 such as a wide band lambda sensor or probe. Basically, the evaluation and operation unit 100 may be applied to any kind of gas sensor such as a NOx-sensor. The evaluation and operation unit 100 is connected by four pins RE, IPE, APE, MES to the electrical wires 201, 202, 203, 204 of electrochemical cells 210, 211 of the gas sensor 200. The electrochemical cells may be a Nernst cell 210 and a pump cell 211. The wires 201, 202, 203, 204 connect the electrochemical cells 210, 211 and a compensation resistor 212 of the gas sensor 200. Depending on the sensor configuration, the used wires may be different, e.g. two cell sensor with 210 and 211 and without the resistor 212, wire 204 is not present or one cell sensor with 211 without both 210 and 212 the wires 201 and 204 are not present. Other combinations are possible as well. The evaluation and operation unit 100 is exemplified by an ASIC reference source 102 to which each of the pins RE, IPE, APE, MES can individually be connected through switches $Swt_{RE}$, $Swt_{IPE}$, $Swt_{APE}$, $Swt_{MES}$ respectively via an optional resistor 101 by means of a controller 103. The ASIC reference source 102 is operable by means of the controller 103. The ASIC reference source 102 may be a potential source. Alternatively, the ASIC reference source 102 may be a current source. Each of the switches $Swt_{RE}$, $Swt_{IPE}$, $Swt_{APE}$, $Swt_{MES}$ may be realized as a switch assembly 104 as will be described in further detail below.

Figure 2:
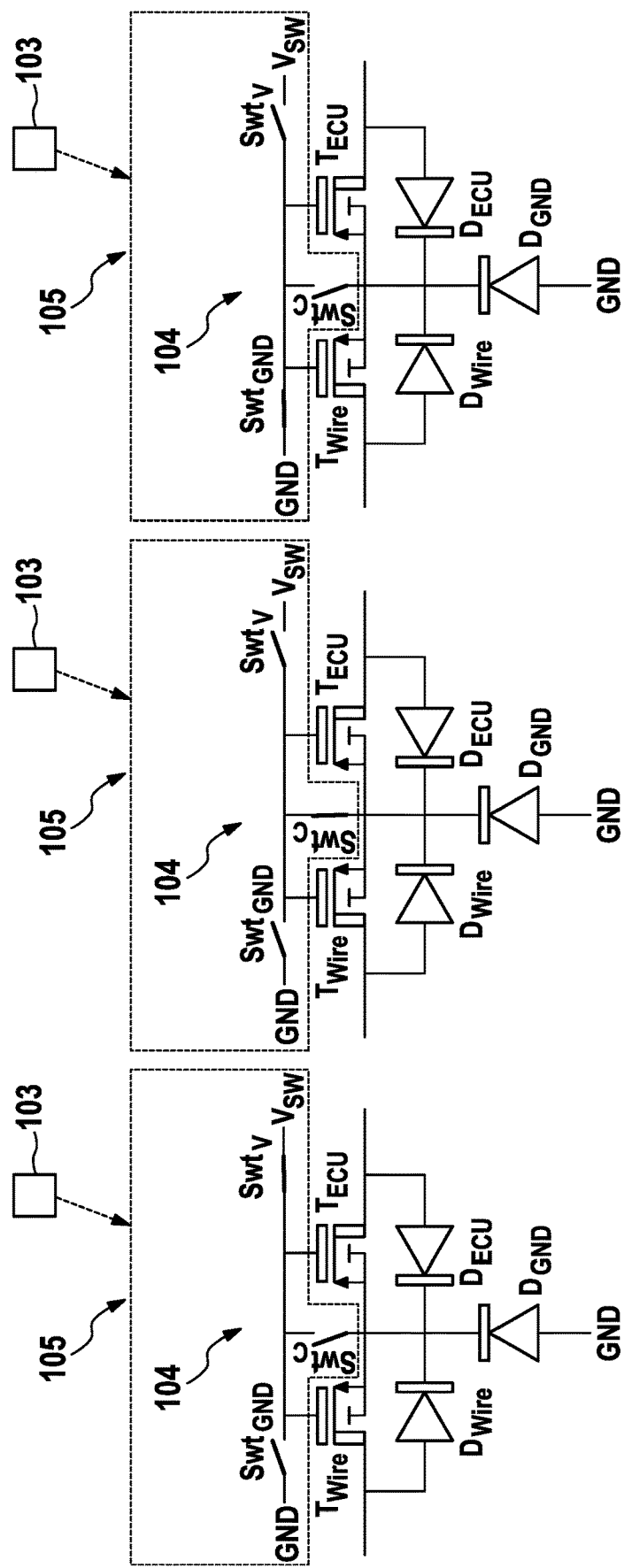
FIGS. 2A to 2C show a switch assembly of the evaluation and operation unit according to a first embodiment in different states.

FIGS. 2A to 2C shows a switch assembly 104 of the evaluation and operation unit 100 according to a first embodiment in different states. The switch assembly 104 is connected to each of the pins RE, IPE, APE, MES. In other words, a separate switch assembly 104 is associated with each of the pins RE, IPE, APE, MES. The switch assembly 104 comprises a first transistor $T_{Wire}$ and a second transistor $T_{ECU}$. Particularly, the drain side of the first transistor $T_{Wire}$ is connected to the pins RE, IPE, APE, MES. In detail, the switch assemblies 104 are realized by diodes or transistors depending on the used semiconductor technology. In order to prevent a current flow in both directions typically two transistors $T_{Wire}$, $T_{ECU}$ are present. This is achieved by orienting the first transistor $T_{Wire}$ and the second transistor $T_{ECU}$ are in opposing directions, meaning that the parasitic diodes of the transistor are looking in opposite ways. Thereby, a current flowing between the right side, such as cables and pins, and the left side, such as the measurement system, with respect to the illustrations of FIGS. 2A to 2C may be effectively stopped up to very high absolute voltages between the pin and the ECU ground, i.e. the ground potential of the controller 103. A switch reference source 105 is connected to a gate side of the first and second transistors $T_{Wire}$, $T_{ECU}$. The switch reference source 105 may be a potential source. Alternatively, the switch reference source 105 may be a current source. The controller 103 is configured to vary the switch reference potential $V_{SW}$ applied to the gate side of the first and second transistors $T_{Wire}$, $T_{ECU}$. Particularly, the switch assembly 104 is configured to allow a limited current flowing through the first transistor $T_{Wire}$ from the ASIC reference source 102 if the potential at the gate side of the first and second transistors $T_{Wire}$, $T_{ECU}$ is at a predetermined voltage between values of an open and closed for switches $Swt_{RE}$, $Swt_{IPE}$, $Swt_{APE}$, and $Swt_{MES}$ over the potential at the source side of the first transistor $T_{Wire}$. Particularly, the controller 103 is configured to set the ASIC reference potential provided by the ASIC reference source 102 to a value larger than the ground of the controller 103 while the switch assembly 104 is in an open state shown in FIG. 2B. The controller 103 is further configured to put the first transistor $T_{Wire}$ in a linear mode provided by the ASIC reference source 102 in relation to a source potential of the first transistor $T_{Wire}$. The evaluation and control unit 100 further comprises at least one comparator (not shown in detail). The controller 103 is configured put the switch assembly 104 in the open state if a short circuit to ground presence or absence is detected by the comparator. The comparator is configured to detect a short circuit to ground at one of the pins RE, IPE, APE, MES if the ASIC reference potential is raised and a potential at that pin RE, IPE, APE, MES exceeds a comparator threshold. The operation of the switch assembly 104 will be described in further detail below with reference to FIGS. 2A to 2C.

As mentioned before, the switch assembly inside an ASIC of the evaluation and operation unit 100 consists of two transistors $T_{Wire}$ and $T_{ECU}$ with a common source. The function of the switch assembly 104 is determined by the switch $Swt_V$ which is normally in a closed state shown in FIG. 2A. In order to set the gate-source voltage of the transistors $T_{Wire}$ and $T_{ECU}$ to zero and the switch assembly 104 to open state, switch $Swt_C$ is closed when $Swt_V$ is open as shown in FIG. 2B. Diodes $D_{GND}$, $D_{Wire}$ or $D_{ECU}$ are intrinsic parasitic diodes of the transistors $T_{Wire}$ and $T_{ECU}$. In some semiconductor technologies some of the diodes might not be present. Forward current through diodes $D_{GND}$, $D_{Wire}$ or $D_{ECU}$ have to be avoided. This is realized by opening $Swt_V$ and closing switch $Swt_C$. In the proposed structure of the switch assembly 104, with switch $Swt_{GND}$, the transistor $T_{Wire}$ is put into the linear mode, where it is high ohmic but conducting, enabling current to flow from the source side to the drain side of the transistor $T_{Wire}$ but limiting it as shown in FIG. 2C. Particularly, in applying a common gate potential $V_{SW}$ below ECU ground to the transistors $T_{Wire}$ and $T_{ECU}$, the total switch formed by the two transistors between the ASIC reference potential and the pin, starts conducting as shown in FIG. 2A, in contrast to when the gates of the transistors are not connected to any potential, as shown in FIG. 2B. This invention additional inserts the possibility to connect the gates of the transistors $T_{Wire}$ and $T_{ECU}$ to a different potential, e.g. ECU ground GND, as shown in FIG. 2C. If the potential at the ECU side of the first transistor $T_{Wire}$, i.e. source of the transistor, is larger than the gate potential of the $T_{Wire}$, e.g. ECU ground, and both are larger than the external voltage at the drain of the first transistor $T_{Wire}$, then the first transistor $T_{Wire}$ is put into linear mode. In this mode, it is neither fully conducting nor fully open, but acts as a resistance, e.g. with 6 kΩ. This means, it allows a current through the transistor, which is much smaller than it would be in the conducting state. This enables charging or discharging external structures like capacitors with time. In effect, the external voltage at the drain of the transistor can rise up to the newly introduced potential at the source of the transistor, e.g. the ECU ground. Additionally, since in this mode an internal ECU voltage is put at the source of the transistors $T_{Wire}$, $T_{ECU}$, no harmful voltages appear. Thus, the internal ECU circuitry is still protected.

The evaluation and operation unit 100 including the specific switch assembly 104 as described above allows treating the, generally temporary, effects of short circuit to ground. The evaluation and operation unit 100, including the specific switch assembly 104, allows raising the voltage at an ECU pin (RE, IPE, APE, MES), if the connection resistance to a fixed voltage source is not too low. The switch assembly 104 is based on current hardware protection structure and does not hinder to pin-point the short circuit to the corresponding wire. The achievement of raising the voltage only affected by coupling effects of short circuits is measureable. With the described structure, further quantitative measurements are allowed once the needed time has passed e.g. with built-in ADC inside the chip. The structure is to be applied to the wide band lambda evaluation circuitry, in order to allow measurements in the case of a short circuit of a wire to a voltage below ECU ground. In conclusion, a pin-pointing of a short circuit to ground is possible.

Figure 3:
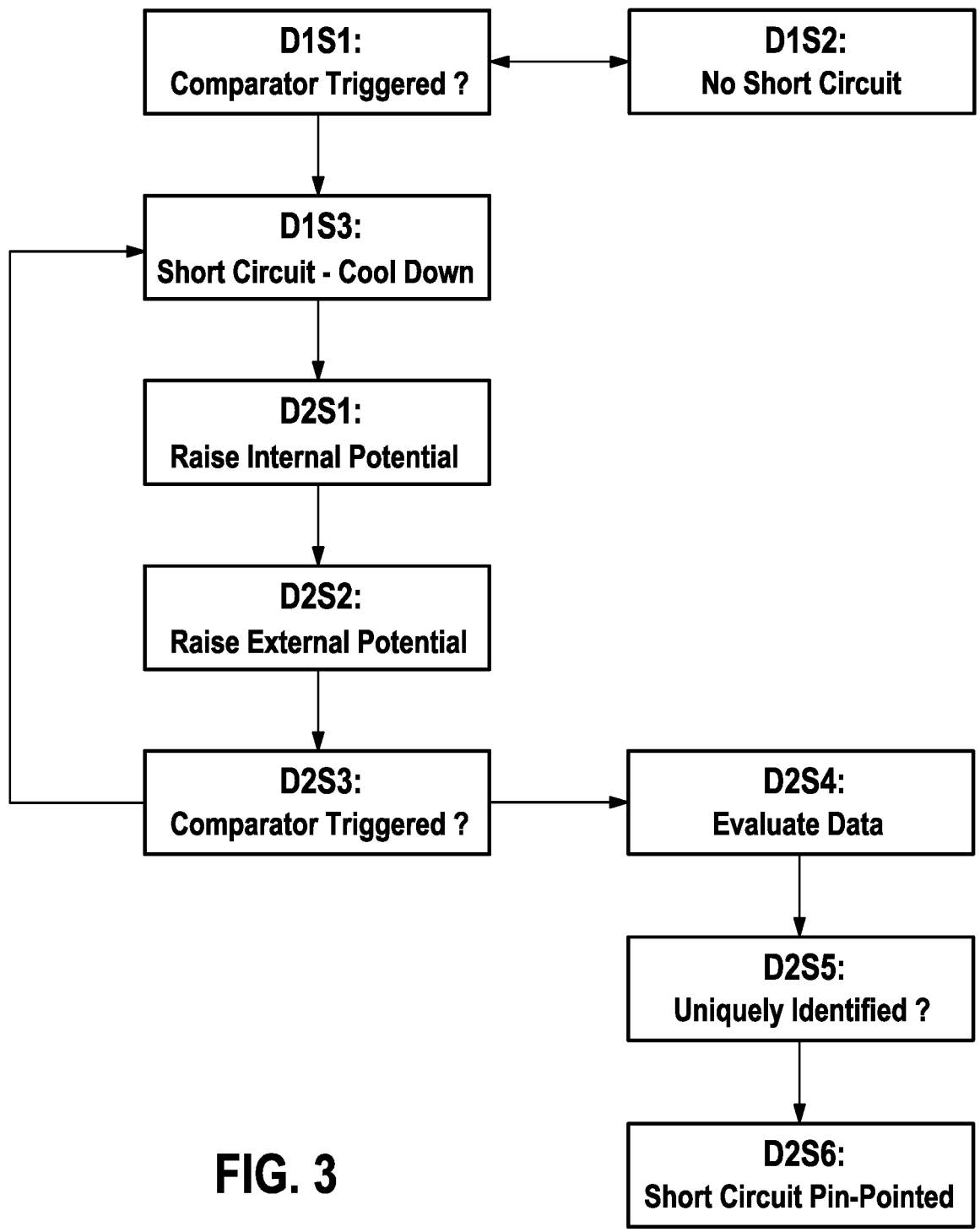
FIG. 3 shows a flow diagram of a method of the present invention.

The method for operating the evaluation and control unit 100 will be described in further detail with reference to FIG. 3. The method can be applied to short circuit to ground diagnosis, exemplified by the following steps. In the first diagnosis step D1S1, a short circuit is detected by additional comparators not shown in FIG. 1: The method starts with a first diagnosis part at a step D1S1. If the potential at the pin RE, IPE, APE or MES is below a threshold, e.g. ECU ground, which is detectable by the comparator, it is concluded that a short circuit to ground is present. In the other case, it is deduced that no short circuit is present in step D1S2 and the first diagnosis step D1S1 is periodically repeated.

In case a short circuit to ground is found to be present, the switches $Swt_{RE}$, $Swt_{IPE}$, $Swt_{APE}$, $Swt_{MES}$ are then opened, i.e. put in the state shown in FIG. 2B, for protection reasons. In this state, the evaluation and operation unit 100 waits until the system has sufficiently cooled down in step D1S3.

In a second diagnosis part, the internal reference potential $V_{SW}$ is switched to a potential well above ECU ground while the switches $Swt_{RE}$, $Swt_{IPE}$, $Swt_{APE}$, $Swt_{MES}$ are still opened in step D2S1. In the following step D2S2, the switches $Swt_{RE}$, $Swt_{IPE}$, $Swt_{APE}$, $Swt_{MES}$ are then put into linear mode, i.e. the state shown in FIG. 2C. Conclusively, all pins RE, IPE, APE, MES which are not directly connected to the short circuit potential will rise, due to the resistances inside the wide band lambda sensor 200. For instance, if wire 201 is shorted to ground, the voltage at pin RE will remain on the short circuit potential while the pins IPE, APE and MES will rise to ECU ground if the sensor resistances are large enough, i.e. if the sensor is cold enough (cf. step D1S3). Alternatively, this step D2S2 can be applied to each pin RE, IPE, APE, MES separately.

After the pin potential is raised, the additional comparators can then be re-evaluated in step D2S3. If the potential at the pin RE, IPE, APE or MES has sufficiently risen, e.g. for all pins except the RE pin, the comparators will not show a voltage too low any more. Concluding, the protection to these specific pins RE, IPE, APE, MES are not necessary anymore. In this case the switches $Swt_{RE}$, $Swt_{IPE}$, $Swt_{APE}$, $Swt_{MES}$ of these pins RE, IPE, APE, MES might be closed, i.e. the state shown in FIG. 2A, in order to obtain additional data to characterize the short circuit in step D2S4.

The next step D2S5 concludes if the pin RE, IPE, APE or MES is uniquely identified. If so, this pin RE, IPE, APE or MES has been pin-pointed to in step D2S6. Whether the pin RE, IPE, APE or MES is unique, can be determined by e.g. by the measurement data of the closed switches $Swt_{RE}$, $Swt_{IPE}$, $Swt_{APE}$, $Swt_{MES}$, e.g. in which direction the pin potential grows or where no data could be retrieved. If the pin was not uniquely identified, the system can be allowed to further cool down as in step D1S3 and/or allowed to take more time for charging/discharging as in step D2S2.

The suggested method can be demonstrated by applying fault patterns to a product while studying the pin voltages at the sensor lines. In case of the used method the voltage at the ECU pin where the fault pattern is not applied is raised. Insight into its data sheet can assure its circuitry, too.

Figure 4:
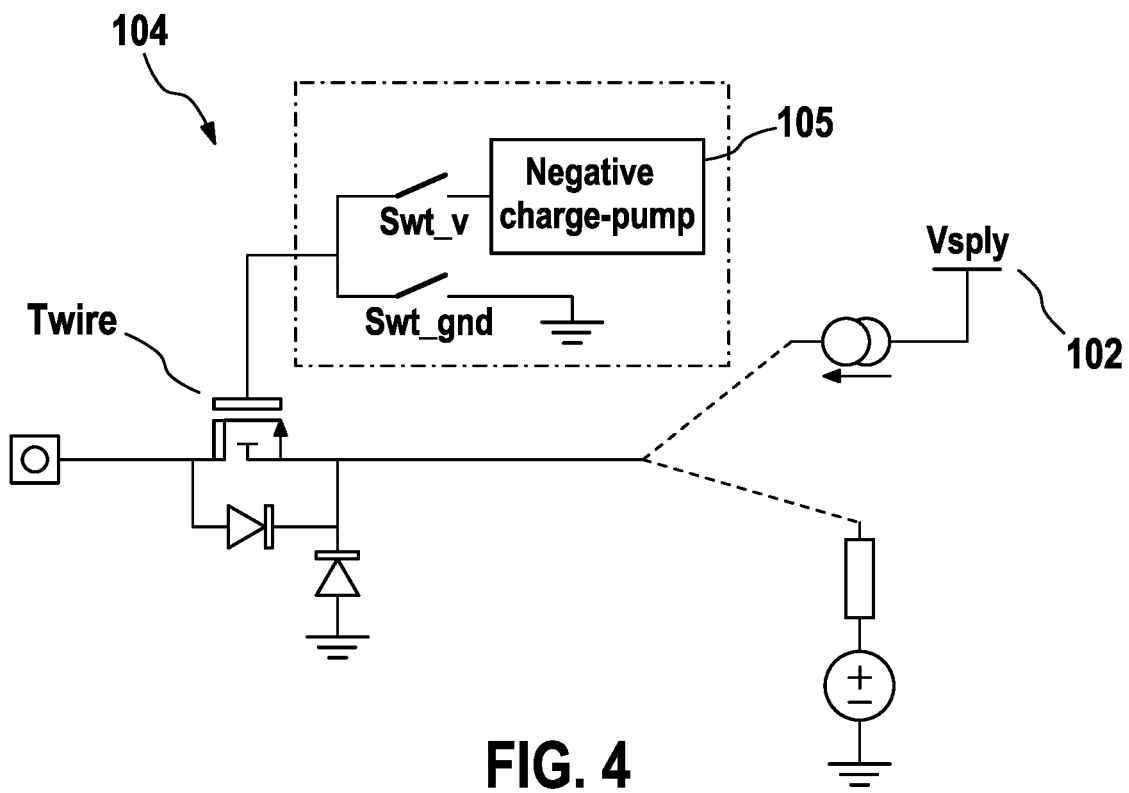
FIG. 4 shows a switch assembly according to a second embodiment and FIG. 5 shows a switch assembly according to a third embodiment.

FIG. 4 shows a switch assembly 104 according to a second embodiment. Hereinafter, only the differences from the first embodiment will be described and like constructional members are indicated by like reference numerals. A basic idea of the switch assembly 104 of the second embodiment is that if there is no requirements that a pin voltage can rise higher than the supply voltage Vsply, it is not mandatory to have the second transistor $T_{ECU}$. As shown in FIG. 4, the switch reference source 105 is connected to a gate side of the first transistor $T_{Wire}$ and the ASIC reference source 102 is connected to the source side of the first transistor $T_{Wire}$. Particularly, the switch $Swt_V$ is located between the switch reference source 105 and gate side of the first transistor $T_{Wire}$ while switch $Swt_{GND}$ is arranged in parallel to the switch $Swt_V$. The switch $Swt_C$ can be omitted.

Figure 5:
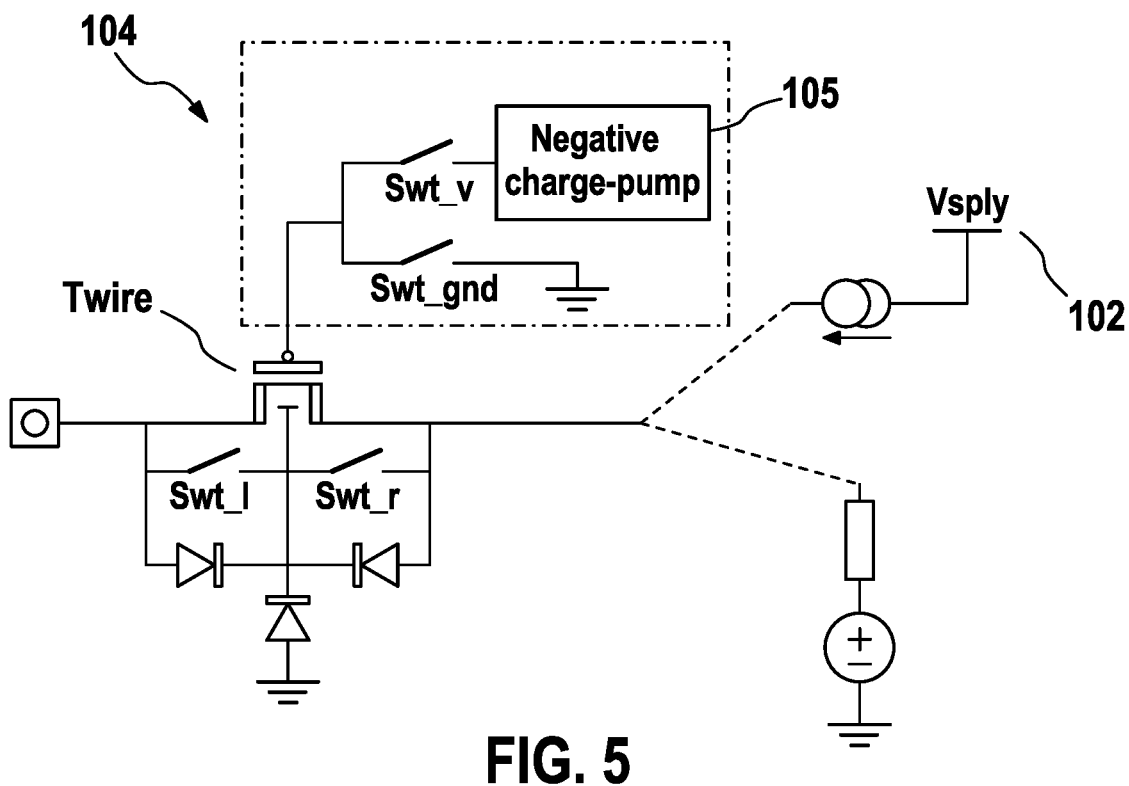

FIG. 5 shows a switch assembly according to a third embodiment. Hereinafter, only the differences from the first embodiment will be described and like constructional members are indicated by like reference numerals. In certain technologies, it is not mandatory to use two transistors. They can be merged into one transistor indicated as the first transistor $T_{Wire}$ with floating bulk that can be connected either to the left or to the right depending on which voltage is higher. As shown in FIG. 5, the switch reference source 105 is connected to a gate side of the first transistor $T_{Wire}$ and the ASIC reference source 102 is connected to the source side of the first transistor $T_{Wire}$. Particularly, the switch $Swt_V$ is located between the switch reference source 105 and gate side of the first transistor $T_{Wire}$ while switch $Swt_{GND}$ is arranged in parallel to the switch $Swt_V$. The switch $Swt_C$ can be omitted. Further, a left switch $Swt_l$ and a right switch $Swt_r$ are shown which are connected in series with one another and are arranged in parallel to the first transistor $T_{Wire}$. FIG. 5 also shows the arrangement of the left switch $Swt_l$ and the right switch $Swt_r$ in parallel with respect to diodes $D_{GND}$, $D_{Wire}$ or $D_{ECU}$.

The invention claimed is:

1. Evaluation and control unit for a gas sensor, comprising:
   pins connectable to electrical wires of electrochemical cells of the gas sensor, a controller,
   an ASIC reference source, wherein the ASIC reference source is operable by means of the controller,
   a switch assembly connected to each of the pins, wherein the switch assembly comprises at least a first transistor, wherein a switch reference source is connected to a gate side of the first transistor and the ASIC reference source is connected to the source side of the first transistor, wherein the controller is configured to vary a switch reference potential applied to the gate side of the first transistor, wherein the switch assembly is configured to allow a limited current flowing to the drain side of the first transistor from the ASIC reference source if the potential at the gate side of the first transistor is at a predetermined voltage between values of an open and closed switch over the potential at the source side of the first transistor.

2. Evaluation and control unit according to claim 1, wherein the controller is configured to switch the ASIC reference potential provided by the ASIC reference source to a value larger than the ground of the controller while the switch assembly is in an open state.

3. Evaluation and control unit according to claim 2, wherein the controller is configured to put the first transistor in a linear mode by varying the switch reference potential in relation to a source potential of the first transistor.

4. Evaluation and control unit according to claim 1, further comprising at least one comparator, wherein the controller is configured put the switch assembly in an open state if a short circuit to ground is detected by the comparator.

5. Evaluation and control unit according to claim 4, wherein the comparator is configured to detect a short circuit to ground presence or absence at one of the pins if the ASIC reference potential is raised and a potential at that pin exceeds a comparator threshold.

6. Evaluation and control unit according to claim 1, wherein the switch assembly further comprises a second transistor, wherein the switch reference source is connected to a gate side of the second transistor and the ASIC reference source is connected to the source side of the second transistor.

7. Evaluation and control unit according to claim 1, wherein the gas sensor is a broadband lambda probe.

* * * * *